United States Patent
Fraser et al.

(10) Patent No.: US 6,478,800 B1
(45) Date of Patent: Nov. 12, 2002

(54) MEDICAL INSTALLATION TOOL

(75) Inventors: Robert D. Fraser, Myrtle Bank (AU); Michael J. O'Neil, West Barnstable, MA (US); Mark Boomer, Providence, RI (US)

(73) Assignee: DePuy AcroMed, Inc., Raynham, MA (US)

( * ) Notice: Subject to any disclaimer, the term of this patent is extended or adjusted under 35 U.S.C. 154(b) by 0 days.

(21) Appl. No.: 09/566,514

(22) Filed: May 8, 2000

(51) Int. Cl.$^7$ ............................................. A61B 17/00
(52) U.S. Cl. ........................ 606/99; 606/90; 623/17.11
(58) Field of Search ............................ 606/86, 90, 99; 623/17.11, 17.16

(56) References Cited

U.S. PATENT DOCUMENTS

| | | | | |
|---|---|---|---|---|
| 3,486,505 A | * | 12/1969 | Morrison | 606/90 |
| 4,545,374 A | * | 10/1985 | Jacobson | 606/61 |
| 4,898,161 A | * | 2/1990 | Grundei | 606/105 |
| 5,020,519 A | * | 6/1991 | Hayes et al. | 128/69 |
| 5,431,658 A | * | 7/1995 | Moskovich | 606/99 |
| 5,800,438 A | * | 9/1998 | Tuke et al. | 606/90 |
| 5,935,151 A | * | 8/1999 | Broughton et al. | 606/241 |
| 5,951,564 A | * | 9/1999 | Schroder et al. | 606/100 |
| 6,080,155 A | * | 6/2000 | Michelson | 606/61 |
| 6,113,602 A | * | 9/2000 | Sand | 606/61 |
| 6,159,215 A | * | 12/2000 | Urbahns et al. | 606/86 |
| 6,168,601 B1 | * | 1/2001 | Martini | 606/90 |

FOREIGN PATENT DOCUMENTS

| | | |
|---|---|---|
| DE | 29901611 U | 4/1999 |
| DE | 29916078 U | 11/1999 |
| DE | 20012549 U | 10/2000 |

OTHER PUBLICATIONS

Technical Manual "Keystone Graft Instruments Anterior Cervical Surgical Technique", Depuy Motech.

* cited by examiner

Primary Examiner—Jeffrey A. Smith
Assistant Examiner—Michael B. Priddy
(74) Attorney, Agent, or Firm—Nutter McClennen & Fish (57) ABSTRACT

A tool for installing an object, such as an artificial disk prosthesis, between adjacent vertebrae includes a pair of opposed levers separated by a fulcrum. Blade tips are disposed at the distal end of the levers. A pusher block is disposed distally of the fulcrum, and upon actuation by forward movement of a pusher rod, the pusher block moves the artificial disk prosthesis distally. The blade tips may be inserted between adjacent vertebral bodies as the disk moves forward thus causing the vertebral bodies to be separated until the disk is disposed therebetween. In one embodiment, the length of the blade tips may be selectively adjusted.

32 Claims, 12 Drawing Sheets

MEDICAL INSTALLATION TOOL

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The invention relates to a tool for inserting prostheses within the body, and more particularly to tools for inserting prostheses, such as artificial disks, within an intervertebral space.

Spinal surgery involves many challenges as the long-term health and mobility of the patient often depends on the surgeon's technique and precision. One type of spinal surgery involves the removal of the natural disk tissue that is located between adjacent vertebral bodies. Procedures are known in which the natural, damaged disk tissue is replaced with an interbody cage or fusion device, or with a disk prosthesis.

The insertion of an article, such as an artificial disk prosthesis, presents the surgeon with several challenges. The adjacent vertebral bodies collapse upon each other once the natural disk tissue is removed. These bodies must be separated to an extent sufficient to enable the placement of the prosthesis. However, if the vertebral bodies are separated, or distracted, to beyond a certain degree, further injury can occur. The disk prosthesis must also be properly positioned between the adjacent vertebral bodies. Over-insertion, or under-insertion of the prosthesis can lead to pain, postural problems and/or limited mobility or freedom of movement.

Specialized tools have been developed to facilitate the placement of devices, such as disk prosthesis, between adjacent vertebral bodies of a patient's spine. Among the known tools for performing such procedures are separate spinal distractors and insertion devices. The use of separate tools to distract the vertebral bodies and insert a disk prosthesis or graft can prove cumbersome. Further, the use of some distractors can cause over-distraction of the vertebral bodies.

Exemplary devices for installing prosthesis and/or grafts between vertebral bodies are disclosed in U.S. Pat. Nos. 5,431,658 and 5,505,732. U.S. Pat. No. 5,431,658 discloses a facilitator device for the insertion of bone grafts between two adjacent vertebrae. The disclosed tool has two flat, tong-like guides that distract the vertebrae as a screw-type inserter forces the graft between the distracted vertebrae. U.S. Pat. No. 5,505,732 discloses an apparatus and a method of inserting spinal implants. The intervertebral space is first distracted and a hollow sleeve having teeth at one end is then driven into the vertebrae that are adjacent the disk space. A drill is then passed through the hollow sleeve, removing the disk and the bone in preparation for receiving the spinal implant, which is then inserted through the sleeve.

Despite existing tools and technologies, there remains a need to provide a device to facilitate the proper and convenient insertion of an object, such as a disk prosthesis, between adjacent vertebral bodies while minimizing the risk of further injury to the patient.

SUMMARY OF THE INVENTION

The present invention provides a device useful for implanting prostheses, such as artificial spinal disks, within a patient in a safe and efficient manner. The installation tool of the invention comprises a pair of opposed levers, each of which has a proximal handle portion and a distal portion. A fulcrum is disposed between the two levers to enable proper operation of the tool. The tool further comprises a pusher block that is positioned between the two levers. The pusher block is selectively movable between an initial location distal of the fulcrum and a final location adjacent the distal end of the levers. A pusher rod, which facilitates movement of a pusher block, has a distal end connected to the pusher block and a proximal, handle end.

Each lever is substantially elongate and the distal portion of each lever comprises an outwardly facing surface that terminates distally in a stop surface and an inwardly facing surface that extends distally beyond the stop surface. Preferably, the outwardly facing surface of each lever is substantially smooth. In one embodiment the stop surface of each lever defines a distal facing wall that is adapted to abut a vertebral body to facilitate proper installation of an artificial disk.

Each lever has opposed side walls and each side wall has a track defined therein. The cross section of each lever may be in the form of an I-shape or a T-shape, and each track in the lever side walls has opposed rails that are separated by a centrally disposed groove. The pusher block may be configured with upper and lower recesses formed in the upper and lower surfaces thereof, wherein each recess is adapted to seat one of the levers. In this embodiment each of the upper and lower recesses has opposed, substantially vertical walls that are separated by a substantially horizontal base wall. Each of the vertical side walls that define the recess of the pusher block preferably has, on an inner surface thereof, a protruding guide post that is adapted to mount within one of the tracks of the levers.

In one embodiment the handle portion of the levers may include protrusions that facilitate blade extraction using a tool such as a slap hammer or a slap fork. In another embodiment, the distal portion of the levers may be configured to permit adjustment of blade tip length.

The installation tool of the invention can be used in the following manner. Once the natural, damaged disk tissue is removed from a patient and the area is prepared to receive an artificial disk, the artificial disk is loaded between the levers of the installation tool so that a posterior side of the disk abuts a distal end of the pusher block. The distal tip of the levers is then positioned between the vertebral bodies such that the outwardly facing surfaces of each lever contacts opposed vertebral bodies. Once this position is achieved, the pusher rod is advanced distally, causing the pusher block and the artificial disk to likewise move distally along the inner surfaces of the levers. As the artificial disk and the pusher rod move distally, or forward, the levers separate and also cause vertical separation of the adjacent vertebral bodies. In the proper position the distal facing surfaces of the two levers should contact the vertebral bodies. Once such contact is achieved between the distal facing surfaces of the levers and the vertebral bodies, and the artificial disk begins to be positioned between the two vertebral bodies, further forward movement of the pusher block, causes the blade tips of the levers to retract from between the vertebral bodies and to eject the artificial disk. This tool thus enables the proper positioning of the artificial disk between the vertebral bodies, without over-insertion or under-insertion of the artificial disk, while minimizing the degree of distraction of the vertebrae.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The present invention comprises an installation tool that is useful for the efficient and effective placement of an article, such as an artificial disk, between adjacent vertebral bodies. Although the invention is described primarily with reference to being used to install an artificial disk between adjacent vertebral bodies, it is understood that the installation tool of the invention can be used to place other elements between vertebral bodies, or in other locations within a patient's body. Exemplary elements that can be placed between vertebral bodies include, but are not limited to interbody cages, fusion devices, spacers, grafts, and the like.

Figure 1:
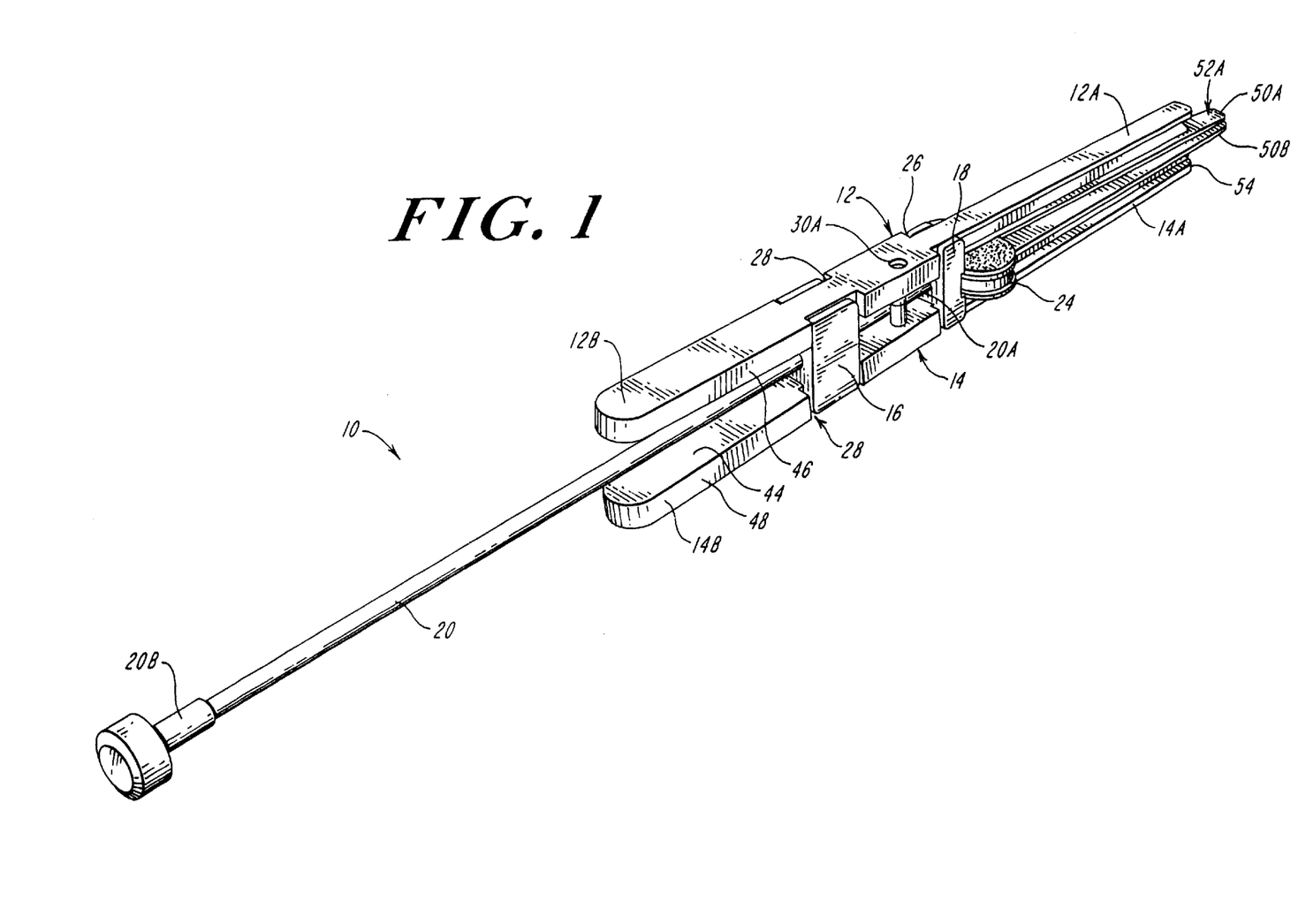
FIG. 1 is a perspective view of an installation tool according to the present invention.
Figure 2:
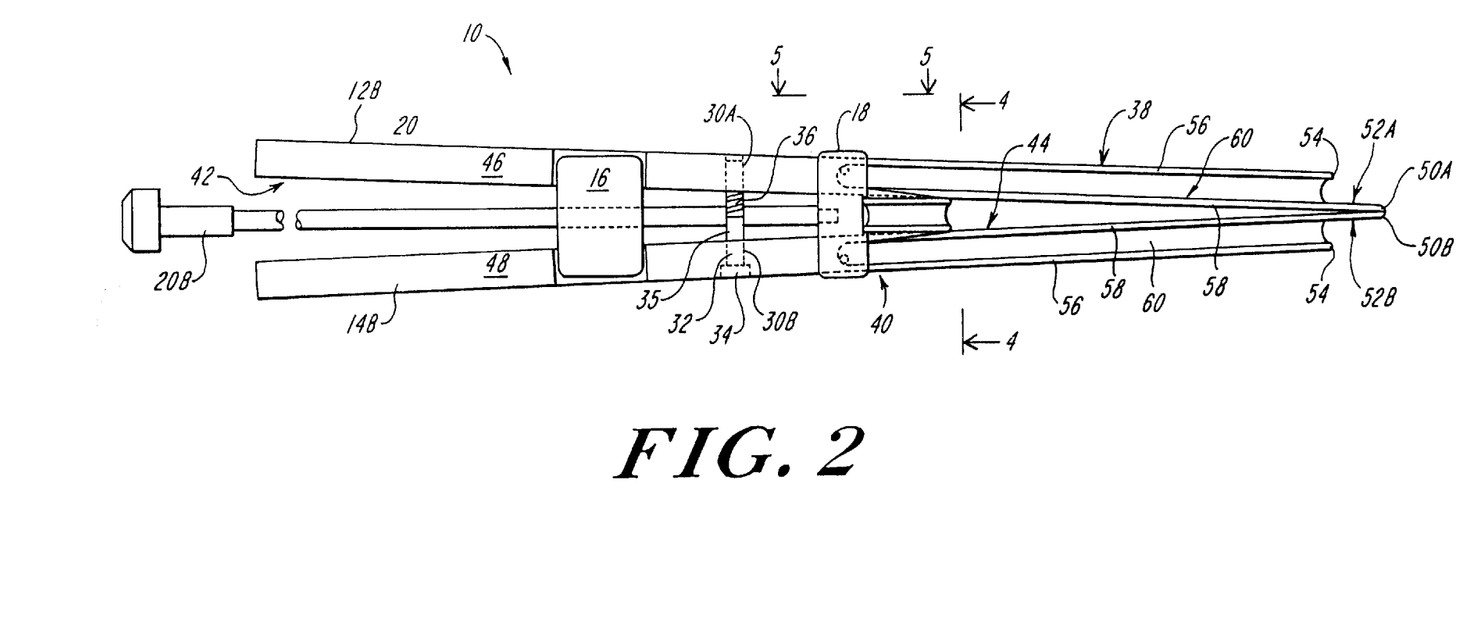
FIG. 2 is a side, elevation view of the tool shown in FIG. 1.
Figure 3:
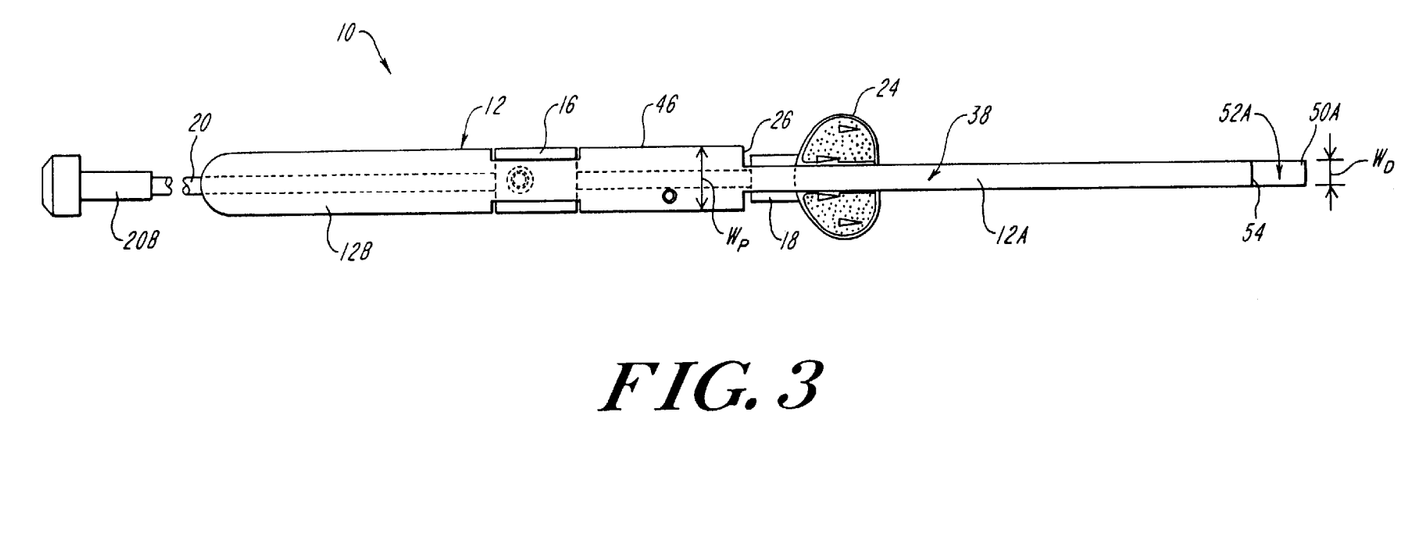
FIG. 3 is a top view of the tool shown in FIG. 1.

As shown in FIGS. 1–3, the installation tool 10 of the invention comprises opposed levers 12, 14 each having a distal portion 12A, 14A and a proximal, handle portion 12B, 14B. Disposed between the levers 12, 14 is a fulcrum 16 and pusher block 18, which is disposed distally of the fulcrum 16. The pusher block 18 is selectively movable from an initial position distal of the fulcrum 16 to a final location adjacent a distal end of the levers. A pusher rod 20, which facilitates selective movement of the pusher block, has a distal end 20A connected to the pusher block and proximal handle end 20B. Although not part of the invention, a prosthesis, such as an artificial disk 24, is positional between the levers, distal of the pusher block 18.

Preferably the levers 12 and 14 are elongate elements that are mirror images of each other. There is no absolute top or bottom of the tool 10 since it is possible to use either surface as a "top" surface. For ease of reference, however, levers will sometimes be described herein with reference to an illustrated orientation. For example, lever 12, and components thereof, may sometimes be referred to as the top, upper, or superior lever while lever 14 may sometimes be referred to as the bottom, lower, or interior lever.

With further reference to FIGS. 1–7, levers 12, 14 include distal 12A, 14A and proximal 12B, 14B ends. The proximal end 12B, 14B of each lever may be of a shape that facilitates convenient grasping and handling of the tool. The proximal end of each lever may comprise approximately one-half of the length of each lever. In one embodiment, a shoulder 26 marks the end of the proximal portion of the tool and the beginning of the distal portion of the tool. As shown in FIGS. 1 and 3, the proximal portion of each lever preferably has a width ($W_p$) that is greater than the width ($W_d$) of the distal portion of each lever.

Figure 6:
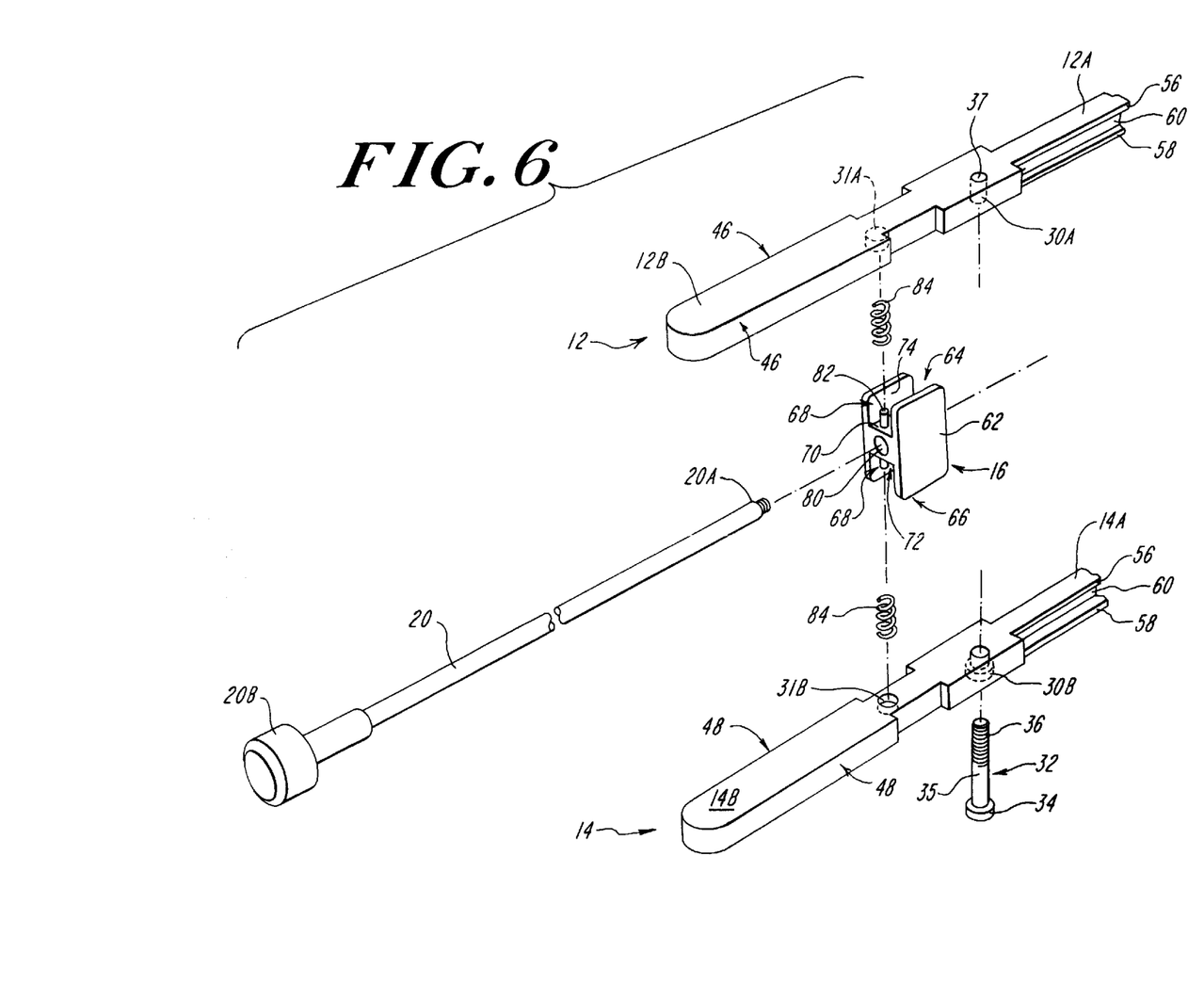
FIG. 6 is an exploded view of a proximal portion of the tool shown in FIG. 1.

The proximal portion 12B of each lever may include an indented region 28 for receiving the fulcrum 16. As shown in FIG. 6, the indented region 28 is in the form of a substantially rectangular cut-out formed on both sides of levers 12B, 14B. This indented region 28 enables the levers to conveniently seat the fulcrum 16, as described below. The recessed region 28 is preferably formed slightly proximally of the shoulder 26. In one embodiment a distal portion 26A of the recessed region 28 begins approximately 10 to 100 mm proximally of shoulder 26. The recessed region generally has a length in the range of about 10 to 40 mm and is recessed by about 1 to 40 mm.

The proximal region of each lever 12B, 14B may also include a bore 30A, 30B which is adapted to seat a bolt 32 that enables control of the spacing between levers so that the pusher block accurately engages the metal portion of the artificial disk. As shown in FIG. 6, bolt 32 includes a head 34 and shaft 35 having a threaded region 36. Preferably, internal threads 36 are formed within bore 30A.

The distal portion of each lever 12A, 14A features outwardly facing surfaces 38, 40 (illustrated as top and bottom surfaces, respectively) and inwardly facing surfaces 42, 44 upon which the artificial disk 24 rides during an installation procedure. The outwardly and inwardly facing surfaces of the lever preferably are substantially smooth. Each lever further includes side surfaces 46, 48.

Distal portions 12A, 14A of levers 12, 14 also have blade tips 50A, 50B formed at the distal ends of the levers. The blade tips are sized and configured to facilitate their placement between vertebral bodies 201, 202. The outwardly facing surfaces 52A, 52B of blade tips may be configured to have surfaces that are beveled or radiused.

Figure 4:
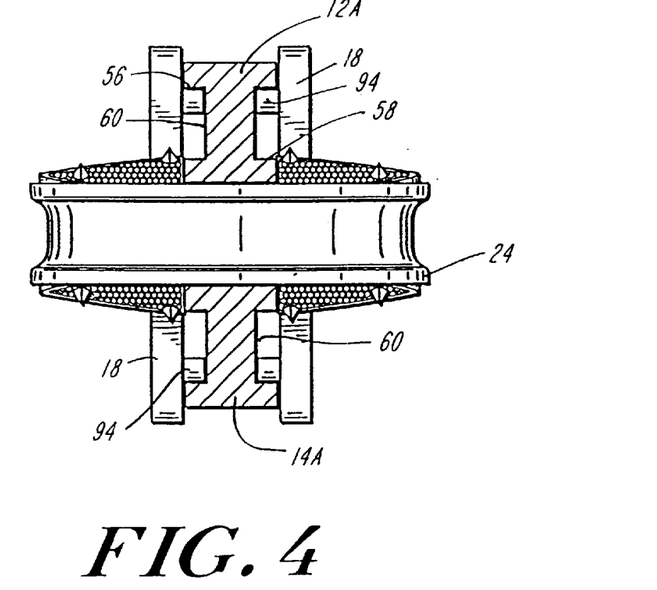
FIG. 4 is a sectional view of the tool shown in FIG. 2, at line 4—4.
Figure 5:
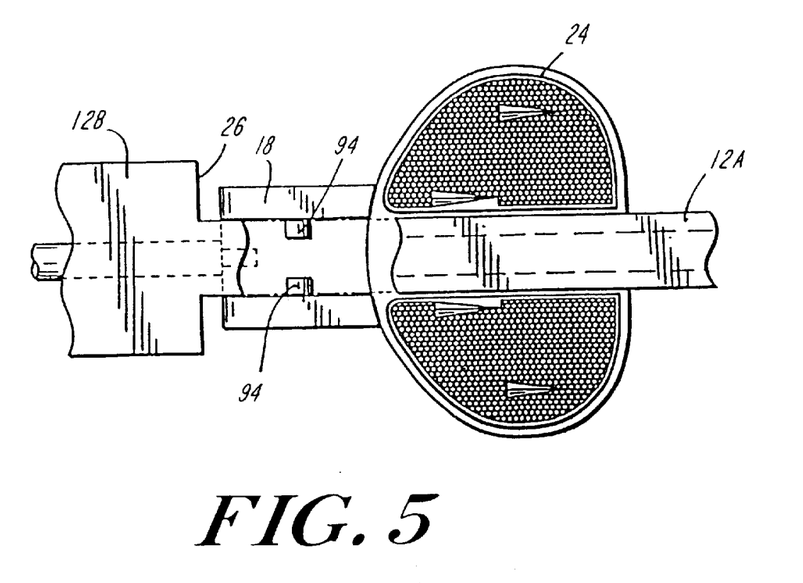
FIG. 5 is a top view of a portion of the tool shown in FIG. 2, at line 5—5.
Figure 7:
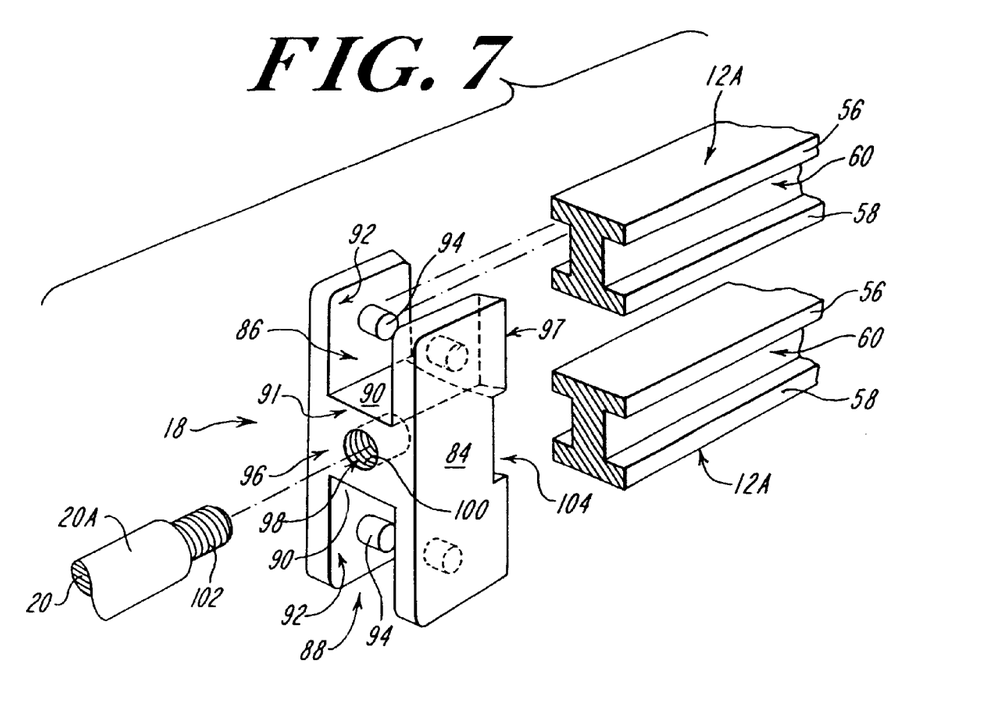
FIG. 7 is an exploded view of a portion of the tool shown in FIG. 1.

The thickness of the levers, measured at the blade tips when the tool is closed, as shown in FIG. 1, is considerably less than the thickness of the levers measured between outwardly facing surfaces 38, 40 when the tool is in the closed position. Preferably, the thickness measured at the blade tips is in the range of about 0.5 to 2 mm. A portion of each lever 12A, 14A, disposed adjacent a proximal end of the blade tips 50A, 50B, includes a stop surface 54. The stop surface 54, which is substantially vertically oriented and distally facing, is adapted to abut a vertebral body during a surgical procedure for installing an element, such as an artificial disk, between adjacent vertebral bodies. The stop surface 54 may assume a variety of configurations. In an exemplary embodiment, shown in FIGS. 2 and 8A–9, the stop surface has a substantially concave profile when viewed in the vertical plane. As shown in FIGS. 1–7 the side surfaces of the distal portions 12A, 14A of the levers 12, 14 may have opposed rails 56, 58, with a recessed track 60 disposed therebetween. The formation of such recessed tracks 60 within the distal side walls of levers 12, 14 causes these elements to have a profile that, as shown in FIGS. 4 and 7, is substantially I-shaped or T-shaped. The rails 56, 58 and track 60, as discussed below, can be effective to facilitate smooth and efficient movement of the pusher block.

One of ordinary skill in the art will appreciate that the size and shape of the levers may vary. Generally, however, the overall length of the levers is about 200 to 400 mm, with proximal portion 12B, 14B (proximal end to shoulder 26) having a length of about 100 to 300 mm and the distal portion 12A, 14A (shoulder 26 to blade tips) having a length of about 100 to 300 mm.

In one embodiment, illustrated in FIGS. 1–3 and 6, the fulcrum 16 is substantially a block-like object having substantially vertical side walls 62. The upper and lower surfaces 64, 66 of fulcrum 16 include recesses or grooves 68, each of which is defined by a base wall 70, 72 and opposed inner side walls 74. A core section 78 lies between the base walls 70 and 72. The core section 78 preferably includes a central bore 80 to allow passage of pusher rod therethrough. In an exemplary embodiment each base wall 70, 72 includes a mounting post 82. As shown in FIG. 6, a biasing element 84, such as a coil spring, may be placed upon each of mounting posts 62 and the mounting posts, in turn, positioned within the bores 31A, 31B of levers 12, 14.

The fulcrum 16 may assume virtually any size and shape that is able to render it effective to separate a substantially intermediate portion of levers while allowing the proximal, handle portion 12B, 14B to be closed together and result in the opening or separation of the distal portion 12A, 14A. Generally, the height of the vertical side walls 62 is in the range of about 20 to 70 mm while the height of the core section 78 is in the range of about 5 to 30 mm. The length of the core section 78 may be about 5 to 40 mm.

One of ordinary skill in the art will further appreciate that the fulcrum may take on a variety of other shapes, sizes and mounting configurations. The embodiment described above is intended to represent one exemplary fulcrum design and mounting configuration.

The bolt 32, as noted above, can be used to adjust the height/spacing of the levers. One of bores 30A, 30B, has internal threads 37 that mate with threaded portion 36 of bolt 32. Tightening or loosening of the bolt will result in increasing or decreasing the spacing/distance between the levers.

Pusher block 18, as best shown in FIG. 7, may be in the form of a substantially block-like object having vertical side walls 84 that define upper and lower recesses 86, 88 wherein each recess is defined by a base wall 90 and opposed inwardly facing side walls 92. Each inwardly facing side wall 92 preferably includes a guide post 94 that is mateable within recessed tracks 60 formed in the distal portion of levers 12A, 14A.

The core section 91 of pusher block 18 is disposed between upper and lower base walls 90. The core section 91 has a proximally facing wall 96 and a distally facing wall 97. As shown in FIG. 7, the proximally facing wall may preferably include a blind bore 98, having internal threads 100. The threads are adapted to mate with complimentary threads formed on a distal end 20A of the pusher rod 20, thereby allowing the pusher rod 20 to positively engage the pusher block 18.

The distal facing wall 97 of the pusher block may include a recessed region 104 that is adapted to nest artificial disk 24. As illustrated, the recessed region 104 has dimensions that enable the artificial disk to fit loosely therein. One of ordinary skill in the art will appreciate that the recessed area should have dimensions slightly greater than the dimensions of the disk so as to avoid a frictional fit that may inhibit free release of the disk from the tool.

Figures 12, 13:
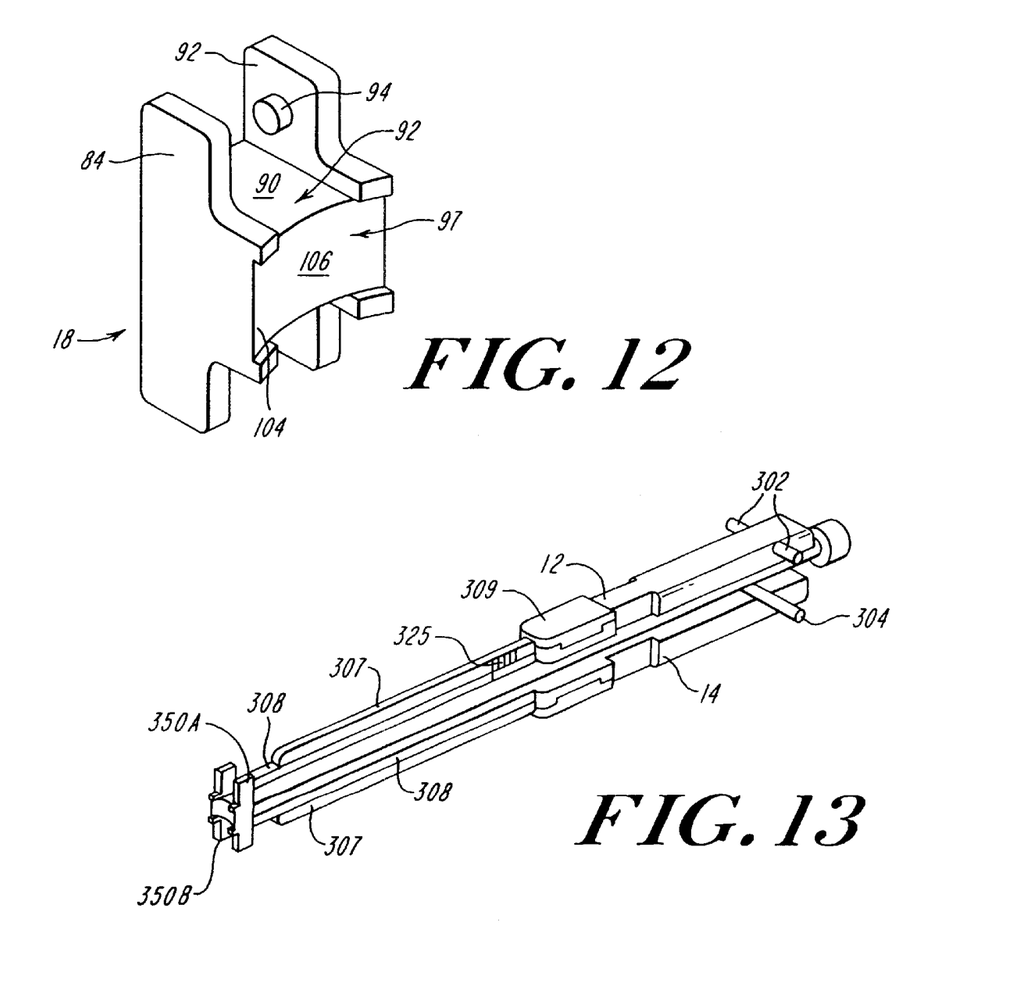
FIG. 12 is perspective view of a pusher block useful with the tool of the present invention.
FIG. 13 is a perspective view of a further embodiment of an installation tool according to the present invention.

In one embodiment, illustrated in FIG. 12, pusher block 18 has a recessed region 104 with a contact wall 106 that has a generally arcuate shape. Preferably, contact wall 106 is substantially concave and well suited to maintaining contact over a substantial surface area of a generally curved (convex) posterior surface of an artificial disk 24.

As noted above, a pusher rod 20 may be utilized to actuate pusher block 18. The pusher rod 20 is preferably an elongate, cylindrical member having a proximal end 20B and a distal end 20A. Preferably, the extreme distal end of the pusher rod includes a threaded region 102. The rod is adapted to be positioned between the proximal ends 12B, 14B of the levers 12, 14 so that it extends through the bore 80 in fulcrum 16. The threaded region 102 of the rod 20 mates with threads 100 formed in bore 98 of pusher block 18. In this way, the rod positively engages the pusher block so that forward and rearward movement of the pusher rod will directly move the pusher block.

Figure 9:
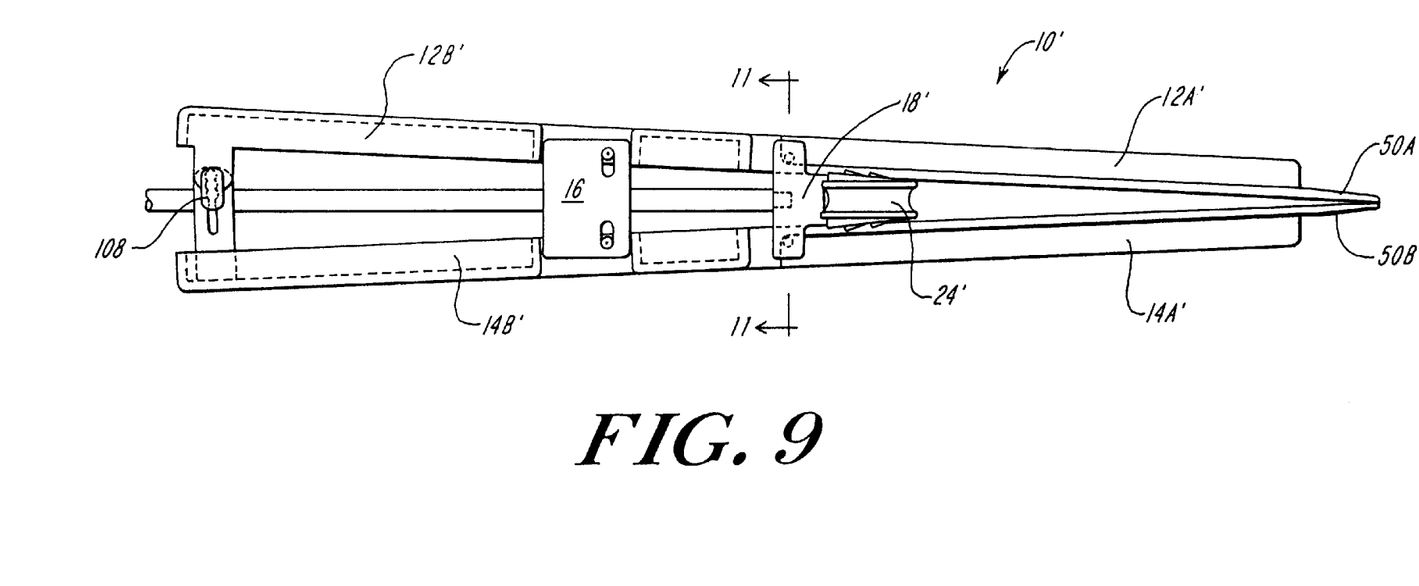
FIG. 9 is a side-elevation view of one embodiment of an installation tool according to the present invention in an initial, unlocked position.
Figure 10:
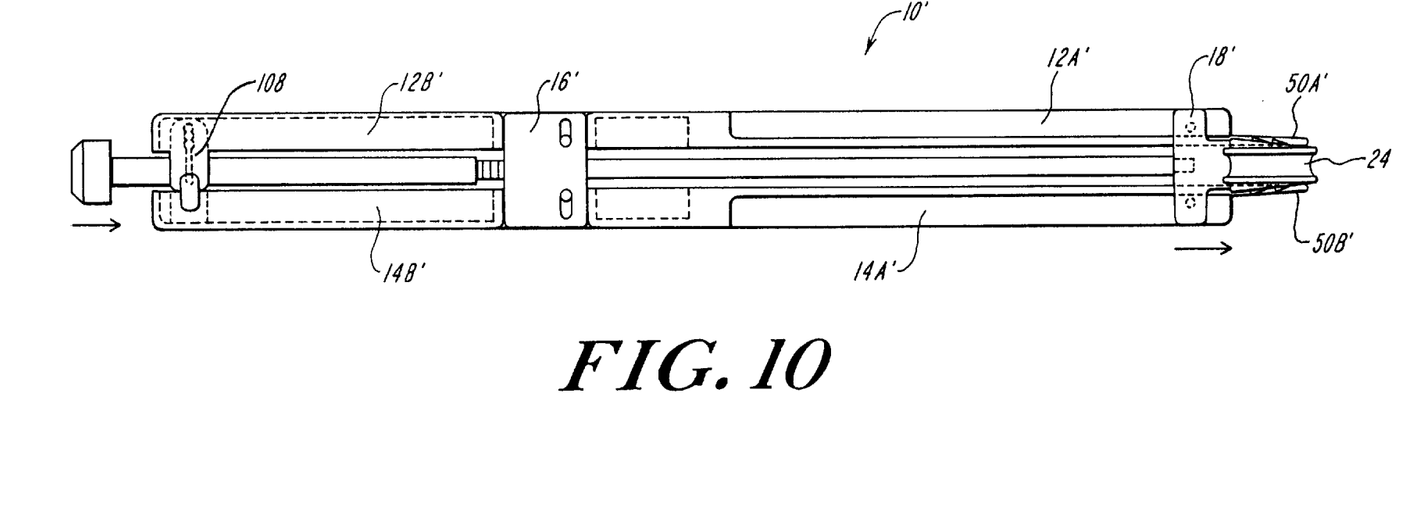
FIG. 10 is a side view of the installation tool of FIG. 9 in a final, locked position.
Figure 11:
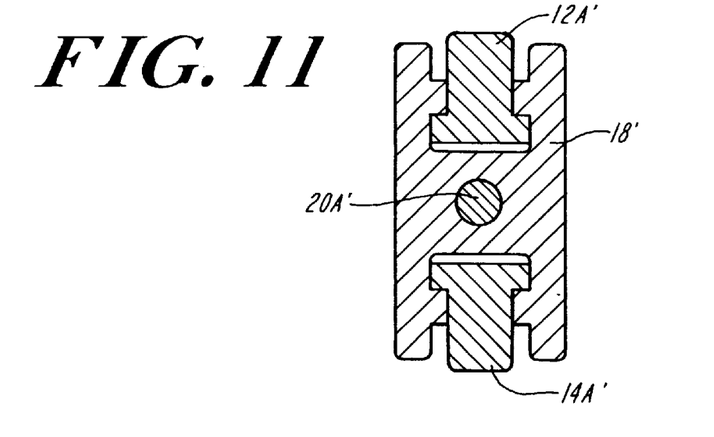
FIG. 11 is a sectional view of the tool shown in FIG. 9, at line 11—11.

FIGS. 9 and 10 illustrate an alternative embodiment in which installation tool 10' includes a locking mechanism 108 in the proximal, handle portion 12B', 14B' of levers 12', 14'. The locking mechanism, which may comprise a latch and groove, simply secures the proximal handle portion of levers in a desired position and prevents complete separation of these elements. FIG. 9 illustrates the tool 10' in a position in which the proximal portion 12B', 14B' of the levers is open or unactuated. The locking mechanism 108 prevents further opening or separation of the proximal portions 12B', 14B' of the levers. However, as shown in FIG. 10, the locking mechanism still allows install a prosthesis, such as artificial disk 24. One benefit of the locking mechanism 108 is that the disk is less likely to become inadvertently dislodged from the tool during pre-surgical installation manipulation of the tool.

FIG. 13 illustrates an embodiment of the invention in which installation tool 300 includes a plurality protrusions 302, 304 formed on proximal or handle portions 312B, 314B of levers 312, 314. Preferably, the protrusions 302, 304 are formed on lateral surfaces of the handle portions. In an exemplary embodiment two protrusions are formed on each of the top and bottom levers 312, 314. Although illustrated as being substantially cylindrical in shape, it is understood that protrusions 302, 304 may take virtually any shape. Protrusions may be useful to facilitate extraction of the blade tips 350A, 350B using a tool such a slap hammer or a slap fork (not shown) in a manner known to one having ordinary skill in the art. The dimensions of protrusions 302, 304 may vary within a wide range. Generally, however, the protrusions 302, 304 extend from the lateral surfaces of levers 312, 314 by a distance of about 3 mm to 50 mm.

Although protrusions 302, 304 are illustrated only with the embodiment of the installation tool shown in FIG. 13, one of ordinary skill in the art will readily appreciate that the protrusions may be present on the handle portions of installation tools constructed according to other embodiments of the invention.

With reference to FIGS. 13–15B, the installation tool 300 may also include a feature which permits selective adjustment of blade tip length (i.e., the distance between the distal end 306 of blade tips 350A, B and stop surface 354).

In such an embodiment the distal portion of each of the levers 312A, 314A has a stop member component 307 and a blade member component 308, which are longitudinally separable with respect to each other. The separability of components 307 and 308 permits the blade tip length to be adjusted by varying the relative positions of components 307, 308.

Figure 14:
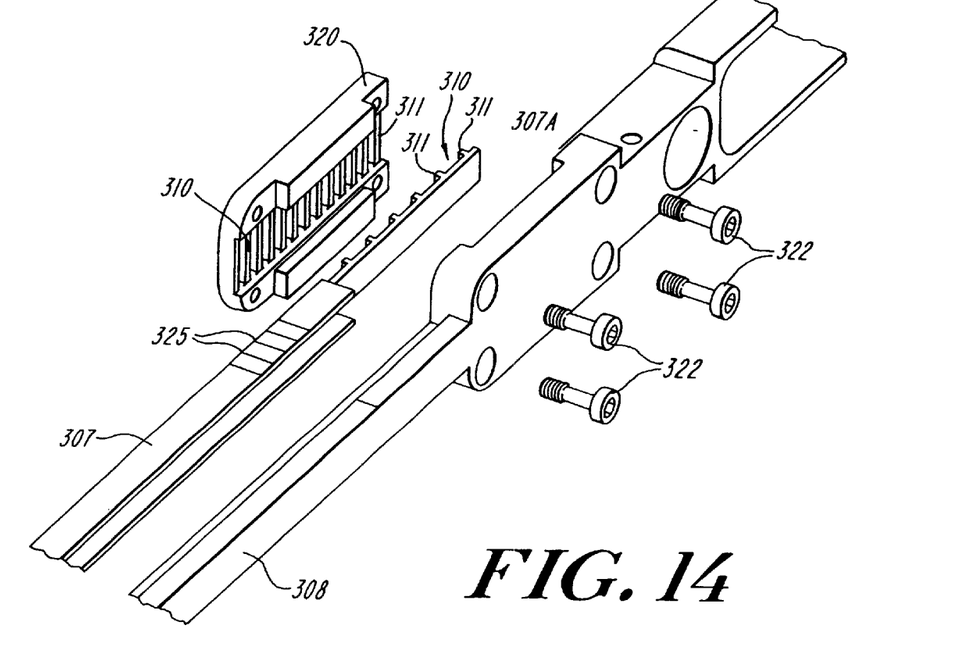
FIG. 14 is an exploded, perspective view of a portion of the installation tool shown in FIG. 13.

As shown in FIGS. 13 and 14 tool 300 includes a junction box 309 which houses and secures the components 307, 308. A portion 307A of the stop member component 307, which mates with the inner surface of the cover 320 of the junction box 309, includes a series of grooves 310 separated by raised ridges 311. Similarly, the abutting, inner surface of the cover 320 of the junction box 309 includes grooves and ridges 310, 311 as well. As further illustrated, the cover 320 is secured to levers 312, 314 by suitable fasteners, such as screws 322. Biasing elements, such as compression springs (not shown) are preferably used to bias the junction box to a position such that the grooves and ridges 310, 311 of the cover 320 and the stop member component 307 mate with and remain firmly secured to one another. As shown in FIG. 14, suitable indicia 325 may be present on the stop member component 307 to indicate the position of the stop member component 307 with respect to the blade member component. Although FIG. 14 only illustrates, in detail, the configuration of lever 12, it is understood that the same construction is used for lever 14.

Figure 15A:
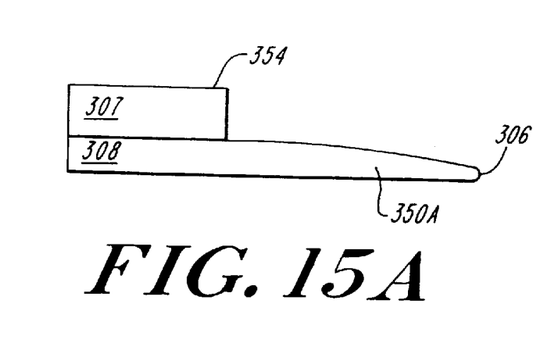
FIG. 15A is a side, elevation view of a portion of the distal end of the installation tool of FIG. 13 in a first position.
Figure 15B:
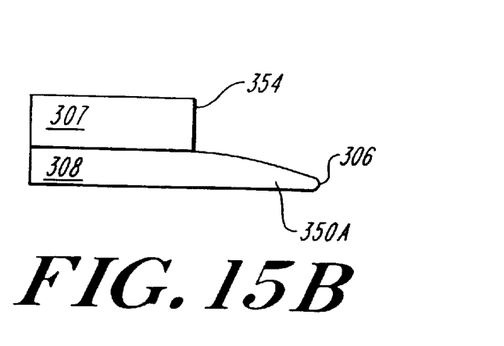
FIG. 15B is a side, elevation view of a portion of the distal end of the installation tool of FIG. 13 in a second position.

The result of this selective adjustability is shown in FIGS. 15A and 15B, in which the blade tip length is greater in FIG. 15A than in FIG. 15B.

Figure 8A:
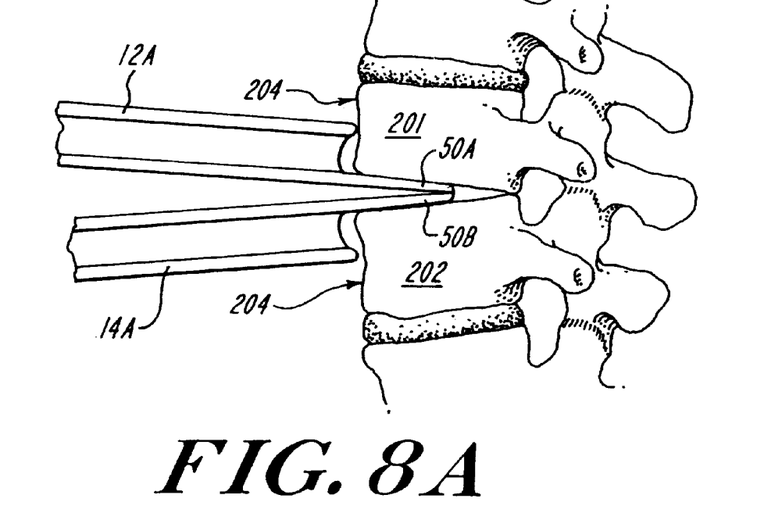
FIGS. 8A–8D illustrate, sequentially, the operation of the installation tool according to the present invention during the installation of an artificial disk.
Figure 8B:
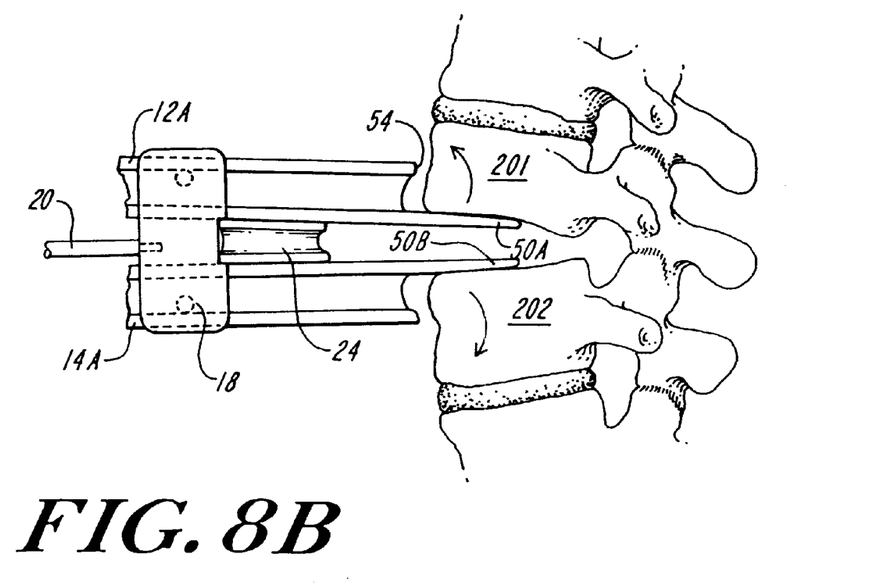
Figure 8C:
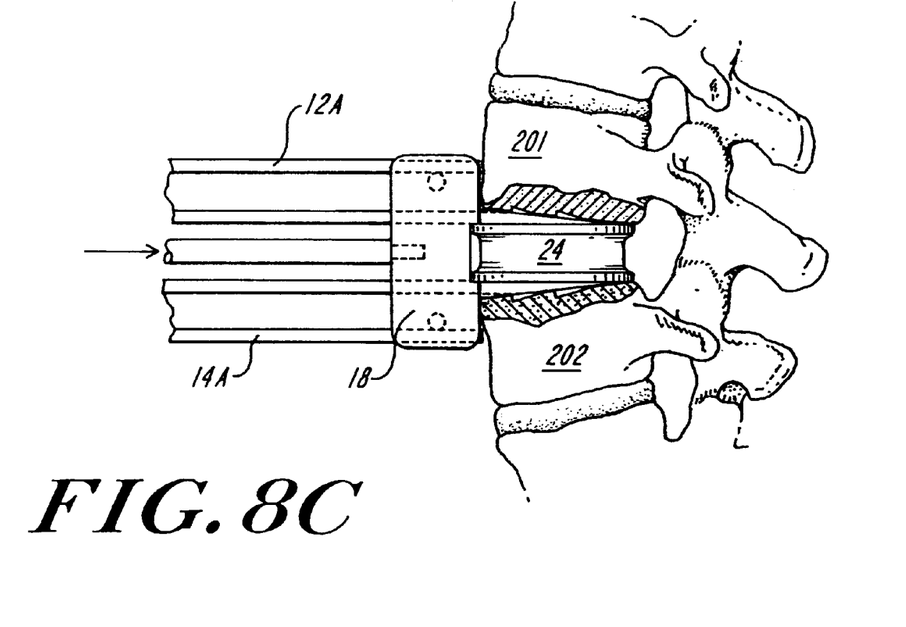
Figure 8D:
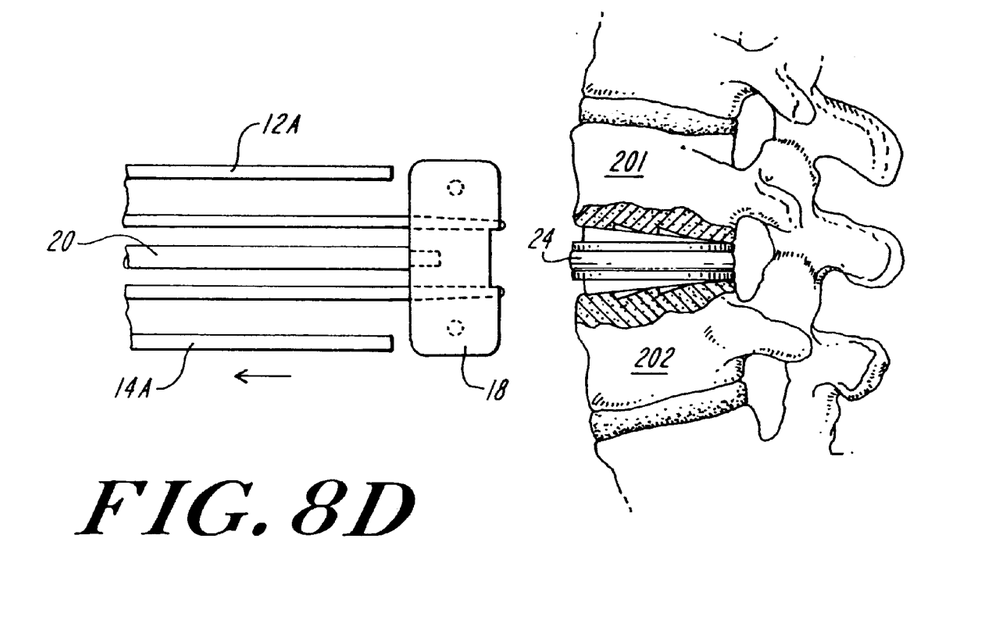

FIGS. 1 and 8A–8D sequentially illustrate the use of tool 10 for the installation of an artificial disk 24. The tool is first assembled as shown in FIG. 1, and with pusher block 18 positioned in its initial position such that its proximally facing wall 96 abuts shoulder 26, the posterior surface 27 of the disk is placed against the distal facing wall 97 of the pusher block. With the handles 12B, 14B in the open position and the blade tips 50A, B closed, the blade tips are wedged between adjacent vertebral bodies 201, 202 to effect slight separation between at least the posterior portions of the vertebral bodies. The blade tips 50A, B should be fully inserted between the vertebral bodies, as shown in FIG. 8A, so as to enable the vertebral stop surface 54 to abut the posterior side 204 of the vertebral bodies 201, 201. The pusher rod 20 is then pushed forward, causing distal movement of the pusher block 18 and artificial disk 24. The forward or distal movement of pusher block 18 and the artificial disk 24 also causes further separation of the blade tips 50A, B and thus further separation of the vertebral bodies 201, 202 as shown in FIG. 8B. Advancement of the pusher block 18 and the artificial disk 24 continues until, as shown in FIG. 8C, the disk is properly installed between adjacent vertebral bodies. FIGS. 8B and 8C illustrate that at all times separation of the vertebral bodies is only effected to the extent necessary to insert the disk. Excessive distraction or separation of the vertebral bodies does not occur because the separation of vertical bodies is caused by the artificial disk and is controlled by the artificial disk thickness dimensions. As the pusher rod 20 continues to be pushed forward upon insertion of the disk the blade tips 50A, B are caused to be retracted from between the vertebral bodies as shown in FIG. 8D.

One of ordinary skill in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entity.

What is claimed is:

1. A medical device installation tool, comprising:
   a pair of opposed levers, each having a proximal, handle portion and a distal portion;
   a fulcrum disposed between the pair of levers;
   a pusher block positioned between the pair of levers and slidably moveable between an initial location distal of the fulcrum and a final location adjacent a distal end of the levers; and
   a pusher rod having a distal end connected to the pusher block and a proximal, handle end.

2. A medical device installation tool, comprising:
   a pair of opposed levers, each having a proximal, handle portion and a distal portion;
   a fulcrum disposed between the pair of levers;
   a pusher block positioned between the pair of levers and selectively moveable between an initial location distal of the fulcrum and a final location adjacent a distal end of the levers; and
   a pusher rod having a distal end connected to the pusher block and a proximal, handle end,
   the device being constructed such that the opposed levers are moveable independent of the pusher block.

3. A medical device installation tool, comprising:
   a pair of separate, opposed levers, each having a proximal, handle portion and a distal portion;
   a fulcrum disposed between the pair of levers;
   a pusher block positioned between the pair of levers and selectively moveable between an initial location distal of the fulcrum and a final location adjacent a distal end of the levers; and
   a pusher rod having a distal end connected to the pusher block and a proximal, handle end.

4. The device of claim 3, wherein each lever is substantially elongate and the distal portion of each lever comprises an outwardly facing surface that terminates distally in a stop surface and an inwardly facing surface that extends distally beyond the stop surface, forming a blade tip.

5. The device of claim 4, wherein each blade tip has a length, extending from the stop surface to a distal end of the blade tip, in the range of about 5 to 50 mm and a thickness in the range of about 0.5 to 10 mm.

6. The device of claim 5, wherein an outwardly facing surface of each blade tip is of a configuration selected from the group consisting of beveled and radiused.

7. The device of claim 4, wherein the stop surface of each lever defines a distally facing stop wall.

8. The device of claim 4, wherein the inner facing wall of each lever, extending to a terminal end of each blade tip, is substantially smooth.

9. The device of claim 4, wherein the pusher block has upper and lower recesses, each adapted to seat one of the levers, wherein each of the upper and lower recesses has opposed, substantially vertical walls separated by a substantially horizontal base wall.

10. The device of claim 9, wherein the depth of each recess of the pusher block is in the range of about 0.5 to 10 mm and the height of the pusher block between the top and bottom recesses is in the range of about 2 to 25 mm.

11. The device of claim 10, wherein a distal facing surface of the pusher block includes an implant seating region.

12. The device of claim 10, wherein the pusher block is effective to separate the levers and the blade tips as it is advanced from the initial location toward the final location.

13. The device of claim 3, wherein the handle portion of the opposed levers includes a locking mechanism effective to prevent unintended, complete separation of the levers.

14. The device of claim 4, wherein the fulcrum has a top recess and a bottom recess, each separated by an intermediate portion having an upper and a lower base wall, the intermediate portion having a bore extending therethrough from a proximal surface to a distal surface of the intermediate portion.

15. The device of claim 14, wherein the upper and lower base walls each include a protruding peg.

16. The device of claim 15, wherein each lever includes a bore formed in the inwardly facing surface of the proximal portion thereof, each bore adapted to receive one of the protruding pegs of the fulcrum.

17. The device of claim 16, wherein the device further includes a pair of coil springs, each of which is adapted to be seated on one of the protruding pegs of the fulcrum.

18. The device of claim 14, wherein the intermediate portion of the fulcrum has a height that exceeds the height of a region of the pusher block between the top and bottom recesses of the pusher block by a distance in the range of about 1 to 20 mm.

19. The device of claim 3, wherein one or more protrusions are formed on a lateral surface of the proximal, handle portion of each of the levers.

20. A device for installing an intervertebral prosthesis, comprising:

separate upper and lower elongate levers, each having a proximal handle portion and a distal portion which includes opposed inwardly facing, prosthesis-contacting surfaces, a stop wall forming a terminal portion of an outer-facing surface of each lever;

a blade tip extending distally beyond the stop wall from the inwardly facing, prosthesis-contacting surface of each lever;

a fulcrum secured between the levers in the proximal portion thereof;

a pusher block positioned between the prosthesis-contacting surfaces of each lever and selectively moveable between an initial position at a proximal end of the distal portion of the levers and a final position adjacent the blade tips; and a pusher rod having a distal end connected to the pusher block and having a proximal, handle end.

21. The device of claim 20, wherein the stop wall is a substantially vertical, distal-facing wall.

22. The device of claim 21, wherein the stop wall is positioned about 5 to about 50 mm proximal of a distal end of the blade tips.

23. The device of claim 20, wherein the blade tips are integral with the prosthesis-contacting surface of the lever.

24. The device of claim 22, wherein each blade tip has smooth inwardly-facing surfaces and outwardly-facing surfaces having a configuration selected from the group consisting of beveled and radiused.

25. The device of claim 20, wherein a protrusion is formed on an outwardly facing surface of the proximal, handle portion of each of the levers.

26. The device of claim 20, wherein the blade tip length, extending from the stop wall to a distal end of the blade tip, is selectively adjustable.

27. A medical device installation tool, comprising:

a pair of opposed levers, each having a proximal, handle portion and a distal portion, wherein the distal portion of each lever has longitudinally separate stop member components and blade member components in which the blade member and stop member components of each lever are moveable with respect to one another;

a fulcrum disposed between the two levers;

a pusher block positioned between the two levers and selectively moveable between an initial location distal of the fulcrum and a final location adjacent a distal end of the levers; and a pusher rod having a distal end connected to the pusher block and a proximal, handle end.

28. The device of claim 27, wherein each lever is substantially elongate and the distal portion of the stop member component of each lever comprises an outwardly facing surface that terminates distally in a stop surface and wherein the blade member component of each lever comprises an inwardly facing surface that extends distally beyond the stop surface, forming a blade tip.

29. The device of claim 28, wherein each blade tip has a length, extending from the stop surface to a distal end of the blade tip, in the range of about 3 to 50 mm and a thickness in the range of about 0.5 to 10 mm.

30. The device of claim 29, wherein the blade tip length is selectively adjustable by moving the blade member and stop member components of each lever with respect to one another.

31. A medical device installation tool, comprising:

a pair of opposed levers, each having a proximal, handle portion and a distal portion;

a fulcrum disposed between the pair of levers;

a pusher block positioned between the pair of levers and selectively moveable between an initial location distal of the fulcrum and a final location adjacent a distal end of the levers; and a pusher rod having a distal end connected to the pusher block and a proximal, handle end, wherein each lever is substantially elongate and the distal portion of each lever comprises an outwardly facing surface that terminates distally in a stop surface and an inwardly facing surface that extends distally beyond the stop surface, forming a blade tip and, wherein the pusher block has upper and lower recesses, each adapted to seat one of the levers, wherein each of the upper and lower recesses has opposed, substantially vertical walls separated by a substantially horizontal base wall.

32. The device of claim 31, wherein a distal facing surface of the pusher block includes an implant seating region.

* * * * *